Figure 1:
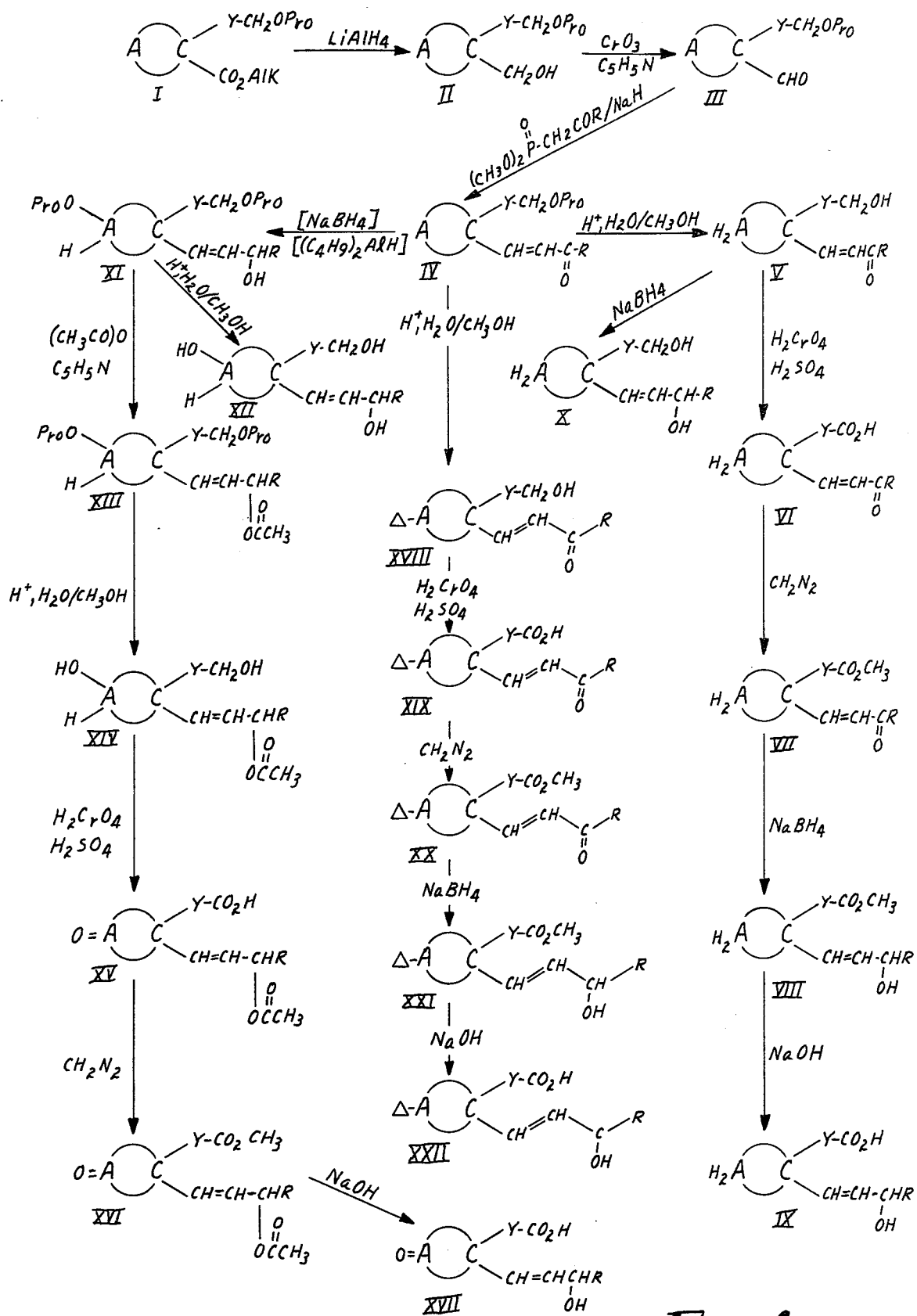

United States Patent [19]

Williams et al.

[11] 4,089,897
[45] May 16, 1978

[54] GEMINAL PROSTAGLANDIN ANALOGS

[75] Inventors: Todd R. Williams, Lake Elmo; Larry M. Sirvio, Cottage Grove, both of Minn.

[73] Assignee: Minnesota Mining and Manufacturing Company, St. Paul, Minn.

[21] Appl. No.: 684,763

[22] Filed: May 10, 1976

[51] Int. Cl.² .................. C07C 177/00; C07C 61/38
[52] U.S. Cl. .................. 260/514 D; 260/345.7 P;
260/345.8 P; 260/345.9 P; 260/413; 260/586 R;
424/317; 424/331; 424/343; 542/426; 560/121;
560/126; 560/231; 260/348.58; 260/348.61;
260/348.57; 568/828; 568/838
[58] Field of Search .......... 260/468 D, 514 D, 348 C, 260/413

[56] References Cited
U.S. PATENT DOCUMENTS 3,954,851  5/1976  Axen .................. 260/514

Primary Examiner—Robert Gerstl
Attorney, Agent, or Firm—Cruzan Alexander; Donald M. Sell; Temple Clayton

[57] ABSTRACT

Geminal prostaglandins (P.G.'s) are synthesized which are represented by the general formula:

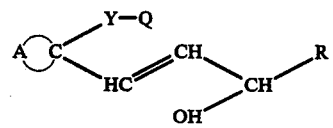

where
A is a 4 or 5 carbon atom ring-completing group $(CH_2)_{1+m}-X-(CH_2)_z$ where $m = 0, 1$ or 2, $z = 0$ or $1, 0 < (m + z) < 3$, and X is $-CH_2-CH_2-$, $-CH_2-CHOH-$,

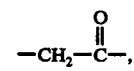

and, when $m = 0$ and $z = 1$, is also $-CH=CH-$ or

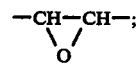

Y is divalent straight chain alkylene of 4 to 8 carbon atoms or

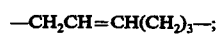

R is alkyl of 4 to 7 carbon atoms;
Q is $-CO_2H$ or $-CH_2OH$ provided that it is not $-CH_2OH$ when X =

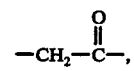

or Y—Q taken together may be heptyl or allyl.

9 Claims, 15 Drawing Figures

GEMINAL PROSTAGLANDIN ANALOGS

This invention relates to a new family of prostaglandin isomers having heretofore unknown structures and to processes and intermediates for making these compounds. In particular this invention relates to geminal prostanoic acids and derivatives.

Naturally occurring prostaglandins are derivatives of prostanoic acid which is an eicosanoic acid in which carbon atoms 8 and 12 are linked to form a 1,2-di-substituted cyclopentane, one substituent of which is a $C_8$ chain and the other is a $C_7$ chain terminated by carboxyl. Numerous analogous compounds have been made in which variations in the structure have been described. The chemistry and pharmacology of these prostaglandins is too vast to review at this place. Reviews are published at frequent intervals and point out the extreme activity in the field in both academic and commercial laboratories.

The nomenclature of natural prostaglandins, all of which have hydroxyl at C-15 and a double bond at C-13,14 makes use of the letters PG and suffixed letters A and B, indicating whether a second double bond in the ring is between carbons 10 and 11 or 8 and 12, and E and F, indicating the presence of 9-oxo-11-hydroxy or 9,11-dihydroxy substituents in the ring. Subscript numbers after the letters indicate the number of double bonds outside the ring. The second is 5,6 and the third 17,18. An additional hydroxyl may appear at position 19. The Greek letter alpha fixed to the subscript number in the F series refers to the (S) configuration of the hydroxyl at carbon 9. Configurations of substituents in natural materials appear to be uniformly the same at positions 8, 12 and 15 and the geometrical configuration at 13,14 is trans, at 5,6 cis and cis at 17,18. It will be recognized that there are numerous possible isomers but there has been considerable success in achieving the necessary stereospecific total syntheses. Natural occurrence is broad but in very low concentrations and isolation is by no means easy.

PGE, PGF, PGA and PGB compounds and derivatives thereof are useful for pharmacological purposes. For example, PGE and PGA compounds cause systemic arterial blood pressure lowering. The E and F series are most potent in causing contraction or relaxation of some smooth muscles. $PGE_1$ shows stimulation of guinea pig ileum at a concentration of 10 ng./ml. and affects the guinea pig colon at less than 0.5 ng./ml. A nanogram (ng) is one thousandth of a microgram, 0.000000001 g.

The most publicized use of the prostaglandins involves the causation of contraction of smooth muscle of the reproductive system in mammals. Here $PGE_2$ causes contraction of the rat uterus at a concentration of 60 ng./ml. These compounds are therefore effective in inducing abortions.

In contrast to the contraction effects noted above, some prostaglandins cause marked relaxation of the smooth muscles of the respiratory system. Here, as measured on cat trachea, PGE is most effective. Correspondingly, the prostaglandins find utility relating to blood platelet aggregation, rates of metabolism, amounts of gastric secretions, diuretic effects, effects on the central nervous system and effects on the ocular system. There is small wonder, then, with the consideration of this myriad of biological activities, that there is extensive interest in the search for analogs processing these or other and more specific activities even at much higher dosage levels. Because the natural prostaglandins are very rapidly metabolized in vivo, longer duration of activity is also sought.

It is a primary aim and object of this invention to provide compounds having prostaglandin type activity, as noted above, and particularly having activity on muscle fibers. Other objects will become evident hereinelsewhere.

In accordance with these and other objects of the invention it has been found that a new series of prostaglandin-like compounds has been synthesized of the general formula

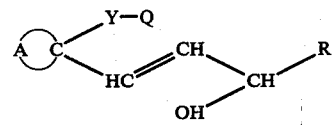

where
A is a 4 or 5 carbon atom ring-completing group $(CH_2)_{1+m}$—X—$(CH_2)_z$ where $m = 0$, 1 or 2, $z = 0$ or 1, $0 < (m+z) < 3$, and X is —$CH_2$—$CH_2$—, —$CH_2$—CHOH—,

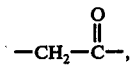

and, when $m = 0$ and $z = 1$, is also —CH=CH— or

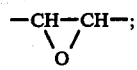

Y is divalent straight chain alkylene of 4 to 8 carbon atoms or

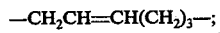

R is alkyl of 4 to 7 carbon atoms;
Q is —$CO_2H$ or —$CH_2OH$ provided that it is not —$CH_2OH$ when X =

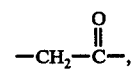

or Y-Q taken together may be heptyl or allyl.

These compounds are termed prostaglandin-like because, as will become clearer herebelow, they generally possess one or more of the several activities associated with natural prostaglandins. They are also termed "geminal prostaglandins" because the two side chains are attached to the same carbon atom, position 8 or 12 in the prostalandin nomenclature when Y is hexamethylene.

In addition to providing the geminal prostaglandins of the invention, many new and useful intermediates are provided which can be used for the production of analogous compounds.

The invention is further explained by the processes and structures set forth in the drawings wherein FIG. 1 is a flow diagram showing reactions of preparation of compounds of the invention by various routes, except for peracid oxidation of cyclopentenes to oxiranes, and FIGS. 2–7 inclusive shown structures of compounds of the invention as follows.

Figure 2:
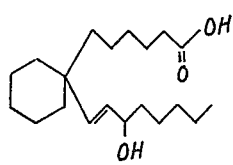

FIG. 2) 6-[1-(3hydroxy-1-octenyl)cyclohexyl]hexanoic acid

Figure 3:
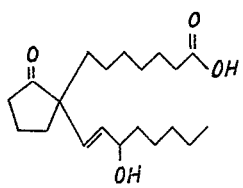

FIG. 3) 7-[1-(3-hydroxy-1-octenyl)-2-oxocyclopentyl]-heptanoic acid

Figure 4:
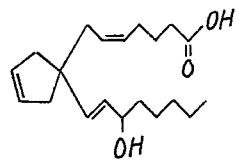

FIG. 4) 7-[1-(3-hydroxy-1-octenyl)-2-cyclopentyl]-5-heptenoic acid

Figure 5:
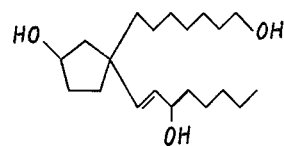

FIG. 5) 7-[1-(3-hydroxy-1-octenyl)-3-hydroxycyclopentyl]heptanol

Figure 6:
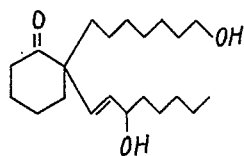

FIG. 6) 9-[1-(3-hydroxy-1-octenyl)-2-oxocyclohexyl]-nonanoic acid

Figure 7:
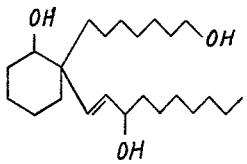

FIG. 7) 7-[1-(3-hydroxy-1-decenyl)-2-hydroxycyclohexyl]heptanol

Figure 8:
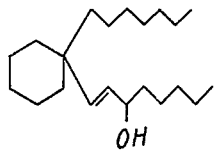

FIG. 8) 1-(1-heptylcyclohexyl)-octen-3-ol

Figure 9:
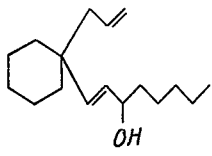

FIG. 9) 1-(1-allylcyclohexyl)-octen-3-ol

Figure 10:
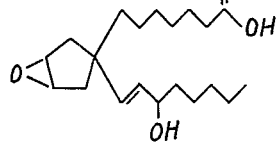

FIG. 10) 7-[1-(3-hydroxy-1-octenyl)-3,4-oxacyclopentyl]heptanoic acid

Figure 11:
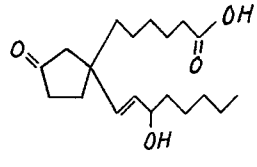

FIG. 11) 6-[1-(3-hydroxy-1-octenyl)-3-oxocyclopentyl]hexanoic acid

Figure 12:
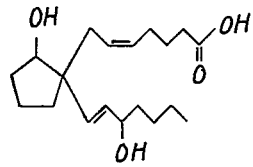

FIG. 12) 7-[1-(3-hydroxy-1-heptenyl)-2-hydroxycyclopentyl]-5-heptenoic acid

Figure 13:
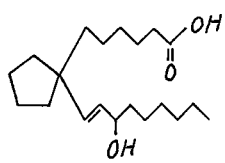

FIG. 13) 6-[1-(3-hydroxy-1-nonenyl)cyclopentyl]-hexanoic acid

Figure 14:
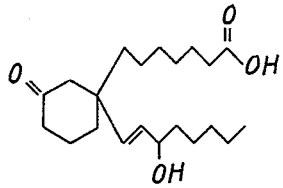

FIG. 14) 7-[1-(3-hydroxy-1-octenyl)-3-oxocyclohexyl]heptanoic acid

Figure 15:
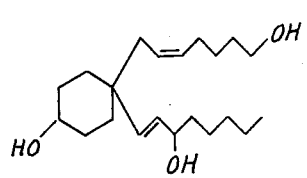

FIG. 15) 7-[1-(3-hydroxy-1-octenyl)-4-hydroxycyclohexyl]-5-heptenol

Generically these compounds are termed geminal prostaglandin analogs, because the two chains are attached to the same carbon atoms, position 8 or 12 in the prostaglandin nomenclature.

Referring particularly to FIG. 1 it will be seen that formulae are provided for compounds designated I through XXII. In these formulae Alk represents a lower alkyl group such as methyl, or ethyl, Pro represents a protective group, suitably a tetrahydropyranyl group or other group stable to strong base and labile in acidic conditions, A, Y and R have their above meanings except as the X group in A above is shown as attached groups, i.e., HO and H for —CH$_2$—CHOH—, OH of which may be protected, O = for

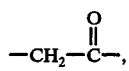

H$_2$ for —CH$_2$—CH$_2$— and Δ for —CH=CH because synthetic routes may be chosen depending on the presence of particular X groups. It will be noted also that the OH forming part of an X group may comprise a protective group, ProO—. The Q group is shown as CH$_2$OPrO in Compound I and modified thereafter. It can obviously be combined with Y in heptyl and allyl groups which would not require the steps needed in modification.

Considering the reactions of FIG. 1 in greater detail it will be seen that the starting compound is an ester I having a protected primary alcohol group. If X is to include a hydroxy or oxo group, I must include some substituent group such as a ProO— group. The ester of Compound I is reduced to the primary alcohol group of Compound II by lithium aluminum hydride. Suitable, but not necessarily exclusive, reaction conditions are illustrated in Examples hereinbelow for this and other reactions set forth in FIG. 1. Compound II is carefully oxidized to the aldehyde, Compound III, using chromium trioxide in pyridine. This is then condensed with the desired dimethyl 2-oxo-alkylphosphonate in the presence of sodium hydride to give the unsaturated ketone Compound IV which may either be reduced to the unsaturated secondary alcohol Compound XI using disobutyl aluminum hydride or sodium borohydride. Alternatively, particularly when no oxygen function is present in A, the protective group on the primary alcohol group (from Compound I) is cleaved using acid in water and methanol to give the ketonic primary alcohol Compound V. It will be noted that in Compound V "H$_2$" is shown attached to A. Although dimethyl 2-oxoheptylphosphonate is (R=C$_5$H$_{11}$) commercially available (Aldrich Chemical Co.), other phosphonates can be synthesized by the methods given in U.S. Pat. No. 3,864,387.

The sequence of reactions used to convert Compound I to Compound V also provides compounds of the invention in which YQ is heptyl or allyl by starting with the appropriate ester.

The sequence of reactions from Compound V leads to products and intermediates which have no oxygen function in the ring, i.e., attached to A. Reduction of the ketone of Compound V using sodium borohydride yields the unsaturated secondary alcohol Compound X which shows prostaglandin-like activity.

Oxidation of the primary alcohol group of Compound V by chromic acid and sulfuric acid yields the unsaturated keto-acid Compound VI which is esterified by diazomethane is the ester Compound VII. The ketone is then reduced by sodium borohydride to the secondary alcohol, Compound VIII, and the ester group saponified by sodium hydroxide to the unsaturated hydroxy acid Compound IX which shows prostaglandin-like activity. By a similar series of reactions the compounds in which A includes a double bond are reacted as Compounds XVIII through XXII.

Compound XI, which contains two protected alcohol groups, is cleaved to a triol, Compound XII, by treatment with acid in water-methanol. Compound XII possesses prostaglandin-like activity. In preparation for selective oxidation, Compound XI is acetylated with acetic anhydride and pyridine to Compound XIII and then the protective groups are removed by treatment with acid in water-methanol to give the diol Compound XIV. Oxidation of Compound XIV by chromic acid and sulfuric acids gives the acetoxy keto acid Compound XV which is esterified to Compound XVI (particularly for ease in purification) and is then saponified to the hydroxy keto acid Compound XVII which shows prostaglandin-like activity.

Although these reactions are shown with particular reactants above and in the Examples, those of skill in the art will recognize variations in procedures and alternative procedures for effecting the desired transformations. It will also be recognized that additional steps may be included to provide desired stereoisomers.

The invention is now further illustrated by specific examples. In the following examples temperatures are in ° C unless otherwise noted. Infra red absorption data are determined without use of solvent (neat) and indicated by "IR" and peaks in reciprocal centimeters (cm$^{-1}$) unless otherwise noted. Proton nuclear magnetic resonance values (designated "nmr") are obtained in CDCl$_3$ and expressed as τ (tau) values.

EXAMPLE 1

The following procedure is illustrative of the procedure for preparing 1-alkyl-cycloalkane-1-carboxylates and 1-hydroxymethyl-1-alkyl cycloalkanes.

A. To a solution of 35 ml. of 2.5 M butyl lithium (87.5 mmol) in 100 ml. dry tetrahydrofuran (THF) at 0° C under an atmosphere of dry nitrogen was added 107 mmol diisopropylamine. After stirring for 15 minutes, the solution was cooled to −70° C (dry ice-acetone) and 50 mmol methyl cyclohexanecarboxylate was added. The solution was maintained at −70° C for 30 minutes and then 75 mmol allyl bromide was added. After being maintained at −70° C for 10 minutes, the solution was warmed to 25° C over 50 minutes and the reaction was quenched by adding water. Excess water was absorbed by sodium sulfate, the slurry was filtered, and the solvent was evaporated at reduced pressure to give 10 g. crude alkylated ester.

B. The crude ester from above was stirred in 250 ml. dry THF while 50 mmol lithium aluminum hydride was added slowly in portions. The resulting slurry was refluxed for 24 hours protected from atmospheric moisture. The reaction was quenched by successive dropwise addition of 1.9 ml. water, 3.0 ml. 10% aqueous sodium hydroxide, and 6.0 ml. water. After one hour of stirring, the white mixture was filtered, the solid washed with ether, and all filtrates combined and evaporated at reduced pressure. The resulting oil was subjected to molecular distillation on a Kugelrohr apparatus at 120° C and 15 mm. Hg to give 7.2 g. (93% for the two steps) of 1-allyl-1-hydroxymethyl cyclohexane. The structure was confirmed by infrared absorption spectra (3350, 1650 cm$^{-1}$) and by conversion to other compounds as described in following examples.

Following the above procedure other compounds were synthesized from the intermediates noted. In each case structures were confirmed by infrared absorption spectra and conversion to other compounds. In some cases nuclear magnetic resonance spectra also were obtained to confirm structures.

C. By replacing allyl bromide in the above procedure with heptyl bromide in the same molar proportions 1-heptyl-1-hydroxymethylcyclohexane was obtained as a liquid (IR 3400 cm$^{-1}$).

D. By employing 6-tetrahydropyranyloxyhexyl bromide (available from 6-bromohexanol and dihydropyran) in place of allyl bromide in the procedures of parts A and B, 1-(6-tetrahydropyranyloxyhexyl)-1-hydroxymethylcyclohexane was obtained as a liquid (IR 3400 cm$^{-1}$).

E. The above procedure was repeated except that methyl cyclopent-3-ene carboxylate (prepared as described by A. H. Schmid and A. W. Wolkoff, J. Org. Chem. 32, 254 (1967)) was used with the 6-tetrahydropyranyloxyhexyl bromide of part D of this example and 1-(6-tetrahydropyranyloxyhexyl)-1-hydroxymethylcyclopent-3-ene was obtained as an oil (IR 3400, 3010 cm$^{-1}$, nmr τ 4.4, 5.4, 6.35, 7.8, 8.5).

F. To 2.8 g. (40 mmol) 2-methyl-2-butene under nitrogen was added 40 ml of 1 molar borane in THF (Aldrich Chemical Co.) with stirring and ice-bath cooling. After 30 minutes 5.0 g. (39.7 mmol) methyl cyclopent-3-ene carboxylate was added dropwise with stirring and ice-bath cooling. After 2 hours at 0° C 6 ml. of 10% sodium hydroxide was added followed by 10 ml. of 30% hydrogen peroxide while maintaining the temperature below 30° C. The mixture was extracted with ether to give 4.6 g. methyl 3-hydroxycyclopentane carboxylate as a liquid (IR 3320, 1730, 1710 cm$^{-1}$; nmr, τ 5.6, 6.3, 6.9, 8.0).

This crude hydroxy ester (2.0 g.) was stirred and a mixture of 1.3 g. dihydropyran and 2 drops phosphorous oxychloride was added. After 2 hrs., 25 ml. ether was added, the solution washed with 100 ml saturated aqueous sodium bicarbonate and the organic phase separated, dried over sodium sulfate and evaporated in vacuo to give 2.0 g. oil. This oil was chromatographed on 100 g. silica gel with 25% ether/petroleum ether eluent to give 1.6 g. methyl 3-tetrahydropyranyloxycyclopentane carboxylate, (IR 1715 cm$^{-1}$; nmr τ 5.4, 5.7, 6.3, 7.1, 8.3).

The procedure of part E was repeated using this substituted ester and the 6-tetrahydropyranyloxyhexyl bromide of Part D of this example, and 1-(6-tetrahydropyranyloxyhexyl)-1-hydroxymethyl-3-tetrahydropyranyloxycyclopentane was obtained as an oil (IR 3400 cm$^{-1}$; nmr τ 5.35, 5.7, 6.35, 7.35, 8.4).

EXAMPLE 2

A. 1-Heptyl-1-hydroxymethylcyclohexane of Example 1, part C, was oxidized with CrO$_3$ and pyridine to the aldehyde, 1-heptyl-1-oxomethylcyclohexane, by following the procedure of Ratcliffe and Rodehurst [J. Org. Chem. 35, 4000 (1970)]. This compound was isolated in ether solution, but not purified, and was alkylated as described in part B below.

B. To a slurry of 11.25 mmol sodium hydride (as a 57% dispersion in mineral oil) in 50 ml. dimethoxyethane (DME) and 5 ml. dimethylsulofoxide was added 11.25 mmol dimethyl 2-oxoheptylphosphonate (available from Aldrich Chemical Co.). After all solid had dissolved, 7.5 mmole of the crude aldehyde from Part A in 5 ml. DME was added, and the reaction mixture was refluxed for 24 hours. Water was added, the solvent removed at reduced pressure, the residue dissolved in ether, and the solution washed with 10% sodium hydroxide until no further color appeared in the aqueous layer and then further washed with water, and saturated sodium chloride solution. After drying over sodium sulfate, the solvent was evaporated and the residue chromatographed on 200 g. neutral silica gel using 15 ml. portions of 10% ethyl acetate in petroleum ether as eluent. The product was found in fractions 20–29 which were combined and evaporated to give 1.43 g. 1-heptyl-1-(3-oxo-1-octenyl)cyclohexane (62% for two steps) as an oil (IR 1600–1720 cm$^{-1}$ (triplet); nmr, τ 3.65, 7.45, 8.6, 9.1).

The above procedure was repeated using the primary alcohols of Example 1 B, D, E and F to give, respectively, the following compounds of parts C, D, E and F, the structures of which were confirmed by infrared and nuclear magnetic resonance spectra.

C. 1-allyl-1-(3-oxo-1-octenyl)cyclohexane (IR 1600–1750 cm$^{-1}$ (triplet); nmr τ 3.6, 4.2, 4.9, 7–8.9, 9.1).

D. 1-(6-tetrahydropyranyloxyhexyl)-1-(3-oxo-1-octenyl)cyclohexane (IR 1600–1700 cm$^{-1}$ (triplet); nmr τ 3.6, 5.4, 6.3, 7.4, 8.6, 9.1).

E. 1-(6-tetrahydropyranyloxyhexyl)-1-(3-oxo-1-octenyl)cyclopent-3-ene (IR 3025, 1600–1700 cm$^{-1}$ (triplet); nmr τ 3.55, 4.4, 5.4, 6.35, 7.5, 8.6, 9.1).

F. 1-(6-tetrahydropyranyloxyhexyl)-1-(3-oxo-1-octenyl)-3-tetrahydropyranyloxycyclopentane (IR 1600–1700 cm$^{-1}$ (triplet); nmr τ 3.6, 5.4, 5.7, 6.35, 7.4, 8.3, 9.1).

EXAMPLE 3

A. A solution of 1.65 mmol 1-heptyl-1-(3-oxo-1-octenyl)cyclohexane (Example 2 part B) in 5 ml. toluene and 10 ml. benzene was cooled to 0° C under a nitrogen atmosphere. To this solution was added over 5 minutes 3.2 mmol diisobutylaluminum hydride (1 M solution in hexane) and the resulting solution was maintained at 0° C for 1 hour. The reaction was quenched by addition of 15 ml. methanol. After stirring for one hour at 25° C, the suspension was filtered through a Celite pad and the filter cake washed well with ether. The combined filtrates were evaporated at reduced pressure and the residual oil chromatographed on 50 g. neutral silica gel using 10% ethyl acetate in petroleum ether and then 15% ethyl acetate in petroleum ether as eluent, taking 15 ml. fractions. Fractions #10-14 were combined to give 0.2 g. pure racemic 1-heptyl-1-(3-hydroxy-1-octenyl)cyclohexane characterized by proton nuclear magnetic resonance ($\tau$ 4.65, 5.9, 8.3–8.9, 9.1).

The ketones of Example 2 parts C, D, E and F are reduced to the respective racemic mixtures of alcohols by the above procedure as follows:

B. 1-allyl-1-(3-hydroxy-1-octenyl)cyclohexane.

C. 1-(6-tetrahydropyranyloxyhexyl)-1-(3-hydroxy-1-octenyl)cyclohexane (IR 3450 cm$^{-1}$; nmr $\tau$ 4.6, 5.9, 6.4, 7.5, 8.6, 9.1).

D. 1-(6-tetrahydropyranyloxyhexyl)-1-(3-hydroxy-1-octenyl)cyclopent-3-ene (IR 3450; 3025 cm$^{-1}$; nmr $\tau$ 4.5, 5.4, 6.75, 7.7, 8.6, 9.1).

E. 1-(6-tetrahydropyranyloxyhexyl)-1-(3-hydroxy-1-octenyl)-3-tetrahydropyranyloxycyclopentane (IR 3450 cm$^{-1}$).

As an alternative procedure,

F. Sodium borohydride can be used instead of diisobutyl aluminum hydride. In this procedure a solution of the ketone (1 equivalent) in ethanol or methanol (7.5 ml. per gram ketone) is stirred and cooled to 0° C and a solution of sodium borohydride (2 equivalents) in alcohol (50 ml. per gram) is added in portions over several minutes. The resulting solution is stirred for 60 minutes and then continuously treated with dilute acetic acid until the foaming stops and the pH is about 8. The solvent is removed, the residue partitioned between water and ether, and the ether layer dried over sodium sulfate. Filtration and removal of solvent give the corresponding alcohol, identical with the product obtained by the procedure of part A above.

EXAMPLE 4

This example illustrates the sequence of reactions described in Examples 1–3 inclusive as applied to compounds including a cyclopentanone group. It will be recognized that ethyl cyclopentan-2-one carboxylate is more readily alkylated than the esters used in Example 1 and that milder conditions can be employed.

A. A mixture of 20 mmol 6-tetrahydropyranyloxyhexyl iodide (from dihydropyran and iodohexanol), 25 mmol ethyl cyclopentan-2-one carboxylate, and 40 mmol potassium carbonate was stirred and refluxed with 125 ml. acetone for 18 hours. After cooling to 25° C, 125 ml. ether was added and the solids filtered off. The filtrate was evaporated at reduced pressure, the residue was dissolved in ether, and the solution was washed in succession with saturated sodium bicarbonate, water, and saturated sodium chloride. After drying the organic phase with sodium sulfate and potassium carbonate, the solvent was removed at reduced pressure and the residual oil subjected to molecular distillation at 175° C/0.25 mm. Hg to give 6.1 g. (88%) product. Proton nuclear magnetic resonance and infrared spectra confirmed the structure as being that of 2-carbethoxy-2-(7-tetrahydropyranyloxyhexyl)cyclopentanone (IR 1760, 1740 cm$^{-1}$; nmr $\tau$ 5.35, 5.75, 6.3, 8.1).

B. The ketone from Part A was dissolved in 50 ml. methanol and stirred at 0° C while a solution of 53 mmol sodium borohydride in 50 ml. methanol was added over several minutes. The resulting mixture was stirred at 0° C for 15 minutes and the reaction was then quenched by cautiously adding 20% aqueous acetic acid until all bubbling stopped. The pH at this point was about 8. Most of the solvent was removed at reduced pressure, the residue was partitioned between ether and water, and the organic phase was dried over sodium sulfate and potassium carbonate. Evaporation of the solvent gave 5.45 g. crude oily product, 2-carbethoxy-2-(6-tetrahydropyranyloxyhexyl)-cyclopentanol, which was used directly.

C. The crude alcohol from Part B was treated with 17.5 mmol dihydropyran and 5 drops phosphorous oxychloride at 0° C and let warm to 25° C overnight. The mixture was diluted with ether and washed with 10% sodium hydroxide, saturated sodium bicarbonate and water. After drying over sodium sulfate, the solvent was removed and the residue chromatographed on 600 g. neutral silica gel using 25% ethyl acetate in petroleum ether as eluent. Combination and evaporation of fractions containing product gave 4.7 g. (55% yield for Parts A-C) of 1-carbethoxy-1-(6-tetrahydropyranyloxyhexyl)-2-tetrahydropyranyloxycyclopentane (IR 1730 cm$^{-1}$).

EXAMPLE 5

Following the procedure of Example 1, Part B, 15 mmol of the crude ester prepared in Example 4, Part C, was reduced with lithium aluminum hydride in refluxing THF. The crude alcohol was chromatographed on 600 g. neutral silica gel using 50% ethyl acetate in petroleum ether as eluent and taking 700 ml. fractions. Fraction 3 had 1.36 g. of one isomer (presumably cis relation between alcohol and ether groups on the ring allowing intramolecular hydrogen-bonding and giving a less polar compound), and fractions 4 and 5 had 3.13 g. of the other isomer (presumably trans). The infrared spectra of the isomers (3500 cm$^{-1}$) and the proton nuclear magnetic resonance spectra of the mixture ($\tau$ 5.4, 5.8–6.8, 7.6–8.9) confirmed the structure of this product as 1-hydroxymethyl-1-(6-tetrahydropyranyloxyhexyl)-2-tetrahydropyranyloxycyclopentane.

EXAMPLE 6

Following the procedure in Example 2, the cis-isomer of the alcohol prepared in Example 5 was converted to 1-$\alpha$-(3-oxo-1-octenyl)-1-$\beta$-(6-tetrahydropyranyloxyhexyl)-2-$\alpha$-tetrahydropyranyloxycyclopentane and its enantiomer as a racemic mixture in 70% yield. The structure was confirmed by infrared and proton nuclear magnetic resonance spectra (IR 1600–1750 cm$^{-1}$ (triplet); nmr 3.45, 5.4, 6.4, 7.45, 8.5, 9.1).

EXAMPLE 7

Following the procedure of Example 2 as in Example 6, the trans-isomer of the alcohol prepared in Example 5 was converted to 1-$\beta$-(3-oxo-1-octenyl)-1-$\alpha$-(6-tetrahydropyranyloxyhexyl)-2-$\alpha$-tetrahydropyranyloxycyclopentane and its enantiomer as a racemic mixture in 75% yield having the same spectra as the product obtained in Example 6.

EXAMPLE 8

Following the procedure of Example 3 the ketone prepared in Example 6 was converted to 1-α-(3-hydroxy-1-octenyl)-1-β-(6-tetrahydropyranyloxyhexyl)-2-α-tetrahydropyranyloxycyclopentane and its enantiomer as a racemic mixture.

EXAMPLE 9

Following the procedure used in Example 8 the ketone prepared in Example 7 was also reduced to yield 1-β-(3-hydroxy-1-octenyl)-1-α-(6-tetrahydropyranyloxyhexyl)-2-α-tetrahydropyranyloxycyclopentane and its enantiomer as a racemic mixture.

EXAMPLE 10

The sequence of reactions described in Examples 4 through 9 was repeated starting with 7-tetrahydropyranyloxyheptyl bromide (available from 7-bromoheptanol and dihydropyran) in place of the lower homolog. The product resulting from repeating Examples 8 and 9 was 1-(7-tetrahydropyranyloxyheptyl)-1-(3-hydroxy-1-octenyl)-2-tetrahydropyranyloxycyclopentane.

EXAMPLE 11

The sequence of reactions of Examples 4 through 9 was also repeated starting with 7-tetrahydropyranyloxy-2-heptenyl bromide (available by the process described in French Pat. No. 2,083,654) in place of the saturated lower homolog used in Example 4.

The product obtained as an oil was 1-(7-tetrahydropyranyloxy-2-heptenyl)-1-(3-hydroxy-1-octenyl)-2-tetrahydropyranyloxycyclopentane.

EXAMPLE 12

A. The alcohol prepared in Example 8 was stirred with 80% aqueous acetic acid (25 ml. per gram of alcohol) at 25° C overnight to hydrolyze tetrahydropyranyl groups. The homogenous reactions mixture was diluted with ether, washed with saturated sodium bicarbonate, and dried over sodium sulfate. After removal of solvent the residue was chromatographed on neutral silica gel (100 g. per g. of product) using 7 ml. portions of 5% isopropyl alcohol in ethyl acetate as eluent. Fractions 9–14 contained product and were combined and evaporated to give a 20% yield of 6-[1-α-(3-hydroxy-1-octenyl)-2-α-hydroxycyclopentyl]hexanol as a racemate.

B. Following the same procedure with the product of Example 9 the product was 6-[1-β-(3-hydroxy-1-octenyl)-2-α-hydroxycyclopentyl]hexanol as a racemate.

C. An alternative procedure for cleavage of the tetrahydropyranyl ethers is effected using methanol and an acid catalyst such as oxalic acid or p-toluene sulfonic acid, at room temperature for several hours. The procedure for isolation is the same as in Part A above. Using this procedure, the product of Example 9 was converted into the product of Part B above.

EXAMPLE 13

A. A solution of 1 g. of 1-(6-tetrahydropyranyloxyhexyl)-1-(3-hydroxy-1-octenyl)cyclohexane produced in Example 3, part C, and 10 mg. p-toluene sulfonic acid hydrate in 20 ml. methanol was refluxed for 1.5 hours. The solvent was replaced with ether and the solution was washed with saturated aqueous sodium bicarbonate. After drying over sodium sulfate, the solvent was removed and the residual oil chromatographed on 50 g. neutral silica gel using 1% methanol-30% ethyl acetate-69% petroleum ether as eluent. Fractions (15 ml. each) #44-52 were combined and evaporated to give 0.17 g. product. The structure was determined by infrared (3300 cm$^{-1}$) and proton nmr ($\tau$ 4.6, 5.9, 6.4, 7.5, 8.5, 9.1) spectra to be 6-[1-(3-hydroxy-1-octenyl)cyclohexyl]hexanol.

B. By repeating the same procedure using the corresponding intermediates in Example 3 part D, there was obtained 6-[1-(3-hydroxy-1-octenyl)-3-cyclopentenyl]hexanol, (IR 3300, 3025 cm$^{-1}$; nmr $\tau$ 4.5, 5.9, 6.4, 7.7, 8.1, 8.6, 9.1).

EXAMPLE 14

A. At 0° C, 2 ml. acetic anhydride and 2 ml. pyridine was added to 0.25 g. of 1-(6-tetrahydroyranyloxyhexyl)-1-(3-hydroxy-1-octenyl)cyclohexane (Example 3, part C). The solution was stirred for five hours while it warmed to 25° C. Ether was added and the solution washed in succession with 10% aqueous sodium hydroxide, 2 M hydrochloric acid, 10% sodium hydroxide, and saturated aqueous NaCl. After drying over sodium sulfate, the solvent was removed at reduced pressure to give 0.35 g. crude acetoxy compound.

B. Following the hydrolysis procedure of Example 13, the above 3-acetoxy compound from Part A, was converted to 1-(6-hydroxyhexyl)-1-(3-acetoxy-1-octenyl)cyclohexane, the structure of which was confirmed by the presence of 3500 and 1740 cm$^{-1}$ bands in the infrared spectrum.

C. A solution of 0.45 g. of the above hydroxyacetoxy product in 13 ml. acetone was cooled to 0° C and stirred while 0.92 ml. of a 2.8 M solution of chromic acid in sulfuric acid was added dropwise. The resulting mixture was stirred for one hour at 0° C and then 30 minutes at 25° C. After addition of 50 ml. water, the mixture was extracted with ether. The organic portions were combined and washed once with water and once with saturated sodium chloride. The organic phase was dried over sodium sulfate and evaporated to give 0.47 g. oil. An infrared spectrum of the crude product indicated complete conversion of starting material to 6-[1-(3-acetoxy-1-octenyl)cyclohexyl]hexanoic acid by the appearance of a band at 1710 cm$^{-1}$ in the infrared spectrum.

D. A solution of 0.45 g. acetoxy carboxylic acid product from Part C above in 10 ml. of 0.5 M sodium hydroxide in 5-50-1 methanol-water was stirred under nitrogen for two hours. Cold 2 M hydrochloric acid was added to acidify, and the product was extracted into dichloromethane. After drying over sodium sulfate and evaporation of solvent, the residue was chromatographed on 50 g. acid-washed silica gel (Mallinckrodt CC-4 special) with 30% ethyl acetate in petroleum ether eluent and 15 ml. fractions. Fractions #7–11 were combined and evaporated to give 0.25 g. 6-[1-(3-hydroxy-1-octenyl)cyclohexyl]hexanoic acid (IR 3000 (broad), 1720 cm$^{-1}$; nmr $\tau$ 4.65, 5.9, 7.6, 8.6, 9.1).

EXAMPLE 15

The procedure of the 4 steps of Example 14 are repeated on the cyclopentane of Example 8 to give A. 1-β-(tetrahydropyranyloxyhexyl)-1-α-(3-acetoxy-1-octenyl)-2-α-(tetrahydropyranyloxy)cyclopentane.

B. 6-[1-α-(3-acetoxy-1-octenyl)-2-α-hydroxycyclopentyl]hexanol (IR 3400 and 1745 cm$^{-1}$; nmr τ 4.4–5.3, 6.3, 7.8, 7.95, 8.6, 9.1).

C. 6-[1-(3-acetoxy-1-octenyl)-2-oxo-cyclopentyl]hexanoic acid (IR 1740 cm$^{-1}$ (doublet)).

D. 6-[1-(3-hydroxy-1-octenyl)-2-oxocyclopentyl]hexanoic acid (IR 1725, 1710 cm$^{-1}$; nmr τ 3.7, 4.45, 5.9, 7.7, 8.1, 8.6, 9.1).

EXAMPLE 16

The four steps of Example 14 are repeated employing as starting material the product of Example 9 to give A. 1-α-(6-tetrahydropyranyloxyhexyl)-1-β-(3-acetoxy-1-octenyl)-2-α-tetrahydropyranyloxycyclopentane.

B. 6-[1-β-(3-acetoxy-1-octenyl)-2-α-hydroxycyclopentyl]hexanol.

C. 6-[1-(3-acetoxy-1-octenyl)-2-oxocyclopentyl]hexanoic acid (as in Example 15 C above).

D. 6-[1-(3-hydroxy-1-octenyl)-2-oxocyclopentyl]hexanoic acid as in Example 15D above.

EXAMPLE 17

A. Following the procedure of Example 13 the product of Example 3 E was hydrolyzed to 6-[1-(3-hydroxy-1-octenyl)-3-hydroxycyclopentyl]hexanol (IR 3300 cm$^{-1}$; nmr τ 4.6, 5.65, 5.9, 6.4, 8.5, 9.1).

EXAMPLE 18

A. Following the procedure of Example 14, the product from Example 10 was converted to the following compounds in succession (1) 1-(7-tetrahydropyranyloxyheptyl)-1-(3-acetoxy-1-octenyl)-2-tetrahydropyranyloxy cyclopentane;

(2) 7-[1-(3-acetoxy-1-octenyl)-2-hydroxycyclopentyl]heptanol (IR 3400 and 1720 cm$^{-1}$; nmr τ 4.5, 6.1, 6.35, 8, 8.6, 9.1);

(3) 7-[1-(3-acetoxy-1-octenyl)-2-oxocyclopentyl]heptanoic acid, isolated as the methyl ester after diazomethane treatment (IR 1725 and 1220 cm$^{-1}$; nmr τ 2.7, 4.5, 5.2, 6.3, 7.7, 7.95, 8.6, 9.1).

(4) 7-[1-(3-hydroxy-1-octenyl)-2-oxocyclopentyl]heptanoic acid (IR 3000 (broad) and 1710 (broad) cm$^{-1}$; nmr τ 3.2, 4.4, 5.85, 7.7, 8.1, 8.6, 9.1).

B. Following the procedure of Example 14, the product from Example 11 was converted to the following compounds in succession:

(1) 1-(7-tetrahydropyranyloxy-2-heptenyl)-1-(3-acetoxy-1-octenyl)-2-tetrahydropyranloxy cyclopentane;

(2) 7-[1-(3-acetoxy-1-octenyl)-2-hydroxycyclopentyl]-4-heptenol;

(3) 7-[1-(3-acetoxy-1-octenyl)-2-oxocyclopentyl]-4-heptenoic acid isolated as the methyl ester after diazomethane treatment (IR 1730 and 1230 cm$^{-1}$);

(4) 7-[1-(3-hydroxy-1-octenyl)-2-oxocyclopentyl]-4-heptenoic acid (IR 3000 (broad) and 1710 (broad) cm$^{-1}$; nmr τ 3.2, 4.5, 5.85, 6.45, 7.5–8.8, 9.1).

C. Following the procedure of Example 14, the product from Example 3, part D, was converted to the following compounds in succession:

(1) 1-(6-tetrahydropyranyloxyhexyl)-1-(3-acetoxy-1-octenyl)cyclopent-3-ene (IR 3025, 1740 cm$^{-1}$; nmr τ 4.45, 5.4, 6.4, 7.7, 7.9, 8.6, 9.1).

(2) 6-[1-(3-acetoxy-1-octenyl)-3-cyclopentenyl]hexanol (IR 3450, 3025, 1740, cm$^{-1}$; nmr τ 4.45, 6.4, 7.7, 7.9, 8.6, 9.1).

(3) 6-[1-(3-acetoxy-1-octenyl)-3-cyclopentenyl]hexanoic acid, isolated as the methyl ester after diazomethane treatment (IR 3025, 1740 cm$^{-1}$; nmr τ 4.45, 6.3, 7.7, 7.9, 8.6, 9.1).

(4) 6-[1-(3-hydroxy-1-octenyl)-3-cyclopentenyl]hexanoic acid, isolated as the methyl ester after diazomethane treatment (IR 3450, 3025, 1740 cm$^{-1}$).

EXAMPLE 19

Physiologic Testing

1. Blood platelet aggregation is tested by the procedure of Born and Cross, Journal of Physiology, Vol. 166, page 178 (1963). Using a commercially available nephelometer (available as a Platelet Aggregometer from Chrono-Log Corporation) and attached recorder the rate and intensity of aggregation is measured by following changes in light transmission through platelet-rich plasma (0.5 ml.) equilibrated at 37° C in a siliconized cuvette with stirring bar in the nephelometer. First, the test compound is added at a concentration of $3 \times 10^{-4}$ molar and equilibrated for 2 minutes at 37° c. Then a standard aggregation inducer. e.g., adenonine diphosphate amount known to effect a certain percentage of aggregation is added at a concentration of 2.5 μg/ml. and changes from the known value are noted.

Compounds of Examples 15D, 17, 18B(2) and 18B(4) inhibit aggregation respectively at $10^{-5}$, $5 \times 10^{-5}$, $5 \times 10^{-4}$ and $5 \times 10^{-7}$ g/ml. For comparison, PGE and PGE$_2$ inhibit at $10^{-9}$ and $10^{-7}$ g/ml. respectively and PGA$_2$ stimulates aggregation at $10^{-5}$.

2. Blood pressure effects are measured following the procedure of J. Weeks et al., J. Pharmacy and Pharmaceuticals, Vol. 21, pages 103–108 (1969).

Rats are anesthetized with sodium pentobarbital (50 mg/kg I.P.). Before giving prostaglandin compounds, animals are bilaterally vagotomized and given "pentolinium" at 5 mg/kg. Test compounds are administered intravenously and blood pressure monitored by the femoral artery.

PGE$_2$ and PGA$_2$ lower blood pressure at $10^{-6}$ g/ml. whereas compounds of Examples 3A, 12A, 12B, 13A, 14D and 15D raise blood pressure at the same concentration.

3. Effects on smooth muscle are determined by widely known procedures.

A piece of muscle is suspended in a bath by conventional techniques. A transducer is appended to the muscle allowing a measurement of relaxation or contraction of the muscle tissue. The compound to be tested is introduced to the bath and the compound's effect on the muscle's dimensions is measured. Smooth muscles include the trachea, ileum and uterus.

Compounds of the invention of Examples 3A, 12A, 12B, 13A, 14D, 15D, 18B(2) and 18B(4) are inactive toward tracheal muscle (see test procedure of Dungan et al., J. Pharmacol. Exp. Ther., 164 290 (1968)) at $10^{-5}$ g/ml. PGE$_1$ and PGE$_2$ effect relaxation at $10^{-6}$ and $10^{-7}$ g/ml respectively. The compound of the invention of Example 3B effects contraction at $10^{-5}$ g/ml.

Compounds of the invention of Examples 3A and 15D were inactive at $10^{-5}$ g/ml and of Example 3B at $10^{-6}$ g/ml toward ileum, PGA$_2$ causes contraction of ileum at $10^{-6}$ and compounds of the invention of Examples 12A, 12B, 14D, cause relaxation of ileum at $10^{-5}$ g/ml, and compounds of Examples 18B(2) and 18B(4) cause relaxation at $5 \times 10^{-5}$ g/ml.

Both PGE$_2$ and PGA$_2$ cause contraction of uterine muscle (see test procedure of Gaddum et al., Quart. J. Exp. Physiol. Vol. 40, 49 (1955)) at $10^{-9}$ and $10^{-7}$ g/ml respectively. Compounds of the invention of Examples 3A, 3B and 18B(4) are inactive toward uterine muscle at $10^{-5}$, $10^{-6}$ and $5 \times 10^{-5}$ g/ml respectively. At $10^{-5}$ g/ml compounds of the invention of Examples 12A, 12B, 13A, 14D and 15D cause relaxation of uterine muscle as does the compound of the invention of Example 18B(2) at $2.5 \times 10^{-5}$ g/ml.

What is claimed is:

1. A geminal prostaglandin represented by the formula

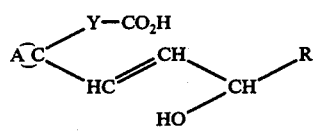

where
A is a 4 or 5 carbon atom ring-completing group $(CH_2)_{1+m}$—X—$(CH_2)_z$ where $m = 0, 1$ or $2$, $z = 0$ or $1$, $0 < (m+z) < 3$, and X is —CH$_2$—CH$_2$—, —CH$_2$—CHOH—,

and, when $m = 0$ and $z = 1$, is also —CH=CH— or

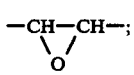

Y is divalent straight chain alkylene of 4 to 8 carbon atoms or

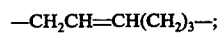

R is alkyl of 4 to 7 carbon atoms.

2. A geminal prostaglandin according to claim 1 represented by the formula:

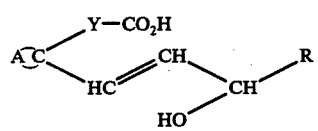

wherein
A is a 4 carbon atom ring-completing group $(CH_2)_{1+m}$—X—$(CH_2)_z$ where $m = 0, 1$ or $2$, $z = 0$ or $1$, $0 < (m+z) < 3$, X is —CH$_2$—CH$_2$—, —CH$_2$—CHOH— or

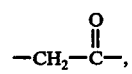

and, when $m = 0$ and $z = 1$, is also —CH=CH— or

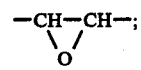

Y is $(CH_2)_6$ and
R is $C_5H_{11}$.

3. A geminal prostaglandin according to claim 1 represented by the formula:

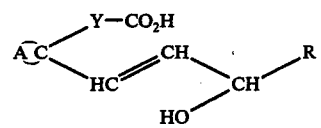

wherein
A is a 4 carbon atom ring-completing group $(CH_2)_{1+m}$—X—$(CH_2)_z$ where $m = 0, 1$ or $2$, $z = 0$ or $1$, $0 < (m+z) < 3$, $x$ is —CH$_2$—CH$_2$—, —CH$_2$—CHOH— or

and, when $m = 0$ and $z = 1$, is also —CH=CH— or

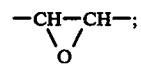

Y is —CH$_2$CH=CH(CH$_2$)$_3$— and
R is $C_5H_{11}$.

4. A geminal prostaglandin according to claim 2 wherein A is

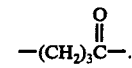

5. A geminal prostaglandin according to claim 2 wherein A is —CH$_2$—CH=CH—CH$_2$—.

6. A geminal prostaglandin according to claim 3 wherein A is

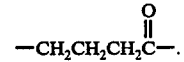

7. A geminal prostaglandin according to claim 3 wherein A is —CH$_2$CH$_2$CH$_2$CHOH—.

8. A geminal prostaglandin according to claim 1 represented by the formula

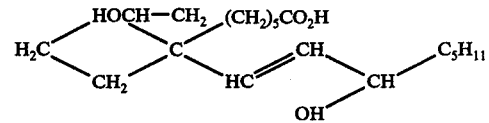

9. A geminal prostaglandin according to claim 1 represented by the formula

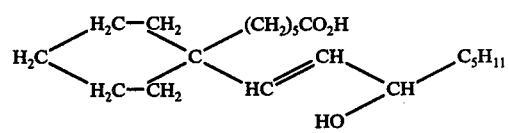

* * * * *